United States Patent
Brunnberg et al.

(10) Patent No.: US 10,376,653 B2
(45) Date of Patent: Aug. 13, 2019

(54) MEDICAMENT DELIVERY DEVICE

(75) Inventors: Lennart Brunnberg, Tyresö (SE);
Anders Wieselblad, Stockholm (SE);
Jonas Norebring, Stockholm (SE)

(73) Assignee: SHL MEDICAL AG, Zug (CH)

( * ) Notice: Subject to any disclaimer, the term of this patent is extended or adjusted under 35 U.S.C. 154(b) by 653 days.

(21) Appl. No.: 13/003,894

(22) PCT Filed: Jun. 18, 2009

(86) PCT No.: PCT/EP2009/057550
§ 371 (c)(1),
(2), (4) Date: Jan. 13, 2011

(87) PCT Pub. No.: WO2010/006870
PCT Pub. Date: Jan. 21, 2010

(65) Prior Publication Data
US 2011/0152781 A1    Jun. 23, 2011

(30) Foreign Application Priority Data
Jul. 15, 2008 (SE) ...................................... 0801692

(51) Int. Cl.
*A61M 5/315* (2006.01)
*A61M 5/24* (2006.01)
(Continued)

(52) U.S. Cl.
CPC .......... *A61M 5/31566* (2013.01); *A61M 5/24* (2013.01); *A61M 5/31* (2013.01);
(Continued)

(58) Field of Classification Search
CPC .. A61M 2005/2433; A61M 2005/2485; A61M 2005/2488; A61M 2005/2492;
(Continued)

(56) References Cited

U.S. PATENT DOCUMENTS 3,503,493 A    3/1970  Nagy
5,377,839 A    1/1995  Relyea et al.
(Continued)

FOREIGN PATENT DOCUMENTS

EP    0941133 B1    4/2004
WO    94/16759 A1   8/1994
(Continued)

OTHER PUBLICATIONS

EPO, Int'l Search Report in PCT/EP2009/057550, dated Oct. 21, 2009.
EPO, Written Opinion in PCT/EP2009/057550, dated Oct. 21, 2009.

*Primary Examiner* — Bhisma Mehta
*Assistant Examiner* — Laura C Schell
(74) *Attorney, Agent, or Firm* — McDonnell Boehnen Hulbert & Berghoff LLP (57) ABSTRACT

The present invention relates to a medicament delivery device comprising a generally tubular distal housing part (10; 110) having opposite proximal and distal ends, wherein third mechanically coded interface means (11; 111) are arranged on its proximal end; a generally tubular proximal housing (20; 120) part having opposite proximal and distal ends and being releasibly connected to said distal housing part, wherein with fourth mechanically coded interface means (22; 122) are arranged on its distal end; a medicament container having a slidable stopper, wherein said container is arranged to be positioned within said proximal housing part; a plunger rod (60; 160) arranged within said distal housing; drive means arranged within said distal housing and being operably connected to said plunger rod for driving said plunger rod and thereby said stopper towards the proximal end of the device; wherein said device further comprises an interface member (50; 150) comprising first (51; 151) and second (52; 152) mechanically coded interface means arranged to match and interact with the third (11; 111)

(Continued)

and the fourth (22; 122) mechanically coded interface means when the distal and the proximal housing parts are connected to each other.

8 Claims, 7 Drawing Sheets

(51) Int. Cl.
    *A61M 5/31*       (2006.01)
    *A61M 15/00*    (2006.01)
    *A61M 11/00*    (2006.01)
    *A61J 7/00*       (2006.01)
    *A61M 5/50*     (2006.01)

(52) U.S. Cl.
    CPC .......... *A61M 5/315* (2013.01); *A61M 5/3129* (2013.01); *A61M 11/007* (2014.02); *A61M 15/0065* (2013.01); *A61J 7/0053* (2013.01); *A61M 5/31525* (2013.01); *A61M 5/5086* (2013.01); *A61M 2005/2407* (2013.01); *A61M 2005/2488* (2013.01); *A61M 2005/3125* (2013.01); *A61M 2005/3126* (2013.01); *A61M 2205/123* (2013.01); *A61M 2205/6045* (2013.01)

(58) Field of Classification Search
    CPC .. A61M 2005/2496; A61M 2005/2437; A61M 2005/244; A61M 2005/2444; A61M 2005/3142; A61M 5/3129–5/3148; A61M 5/31566; A61M 11/007; A61M 5/24; A61M 5/31; A61M 5/315; A61M 15/0065; A61M 5/31525; A61M 5/5086; A61M 2005/3125; A61M 2005/3126; A61M 2205/123; A61M 2205/6045; A61M 5/20–2005/31598

USPC ........................................................ 604/207
See application file for complete search history.

(56) References Cited

U.S. PATENT DOCUMENTS

| | | | |
|---|---|---|---|
| 5,611,783 A | | 3/1997 | Mikkelsen |
| 5,674,204 A | * | 10/1997 | Chanoch ........... A61M 5/31535 604/207 |
| 5,693,027 A | | 12/1997 | Hansen et al. |
| 2003/0004466 A1 | * | 1/2003 | Bitdinger ................ A61M 5/24 604/218 |
| 2004/0030297 A1 | * | 2/2004 | Hegewald ............... A61M 5/24 604/207 |
| 2004/0186442 A1 | * | 9/2004 | Graf ................... A61M 5/31553 604/207 |
| 2008/0097338 A1 | * | 4/2008 | Cheng ..................... A61M 5/24 604/201 |
| 2008/0195057 A1 | * | 8/2008 | Graf ....................... A61M 5/315 604/218 |
| 2010/0042054 A1 | * | 2/2010 | Elahi ....................... A61M 5/24 604/211 |

FOREIGN PATENT DOCUMENTS

| | | | |
|---|---|---|---|
| WO | 03/017915 A1 | | 3/2003 |
| WO | 2008/000827 A1 | | 1/2008 |
| WO | 2008/009645 A1 | | 1/2008 |
| WO | 2008/009646 A1 | | 1/2008 |
| WO | 2008/009647 A1 | | 1/2008 |
| WO | 2008/025772 A1 | | 3/2008 |
| WO | 208/062025 A1 | | 5/2008 |
| WO | 2008/059063 A1 | | 5/2008 |
| WO | WO 2008/059063 | * | 5/2008 |
| WO | WO2008/062025 | * | 5/2008 |
| WO | 2008/074897 A1 | | 6/2008 |

* cited by examiner

MEDICAMENT DELIVERY DEVICE

TECHNICAL FIELD

The present invention relates generally to a medicament delivery device having an interface member comprising identification means.

BACKGROUND ART

Today, there are a large number of patients providing themselves, or being provided by others, with a medicament regimen using a medicament delivery device, such as an inhaler, an injector, or another type of dispensing device including tablet dispensing devices. In many cases, the medicament is arranged, for example, in a container and the like (in case of an inhaler), in a, for example, cartridge (in case of an injector), or, for example, in a blister package in case of a tablet dispensing device. Normally, information regarding the drug or medicament is printed directly on the container or corresponding or on labels attached to them so that the patient or the doctor can read what kind of drug the container is filled with. Hence, there always a risk that an incorrect dosage of the drug or medication is provided in the device with potential lethal implications due to, for example, the fact that the patient misinterprets or misreads the label of the container.

For example, many inhalers present on the market have the medicament arranged in containers and the like, containing a number of doses of medicament. In some cases, the containers or canisters and the inhalers are adapted so that the containers can be replaced, e.g. replacing an empty container with a full. For example, the containers of aerosol-driven inhalers are in the form of cylindrical metal canisters that are placed in a space within the inhaler. Some powder inhalers utilize ampoules or a plurality of blisters arranged on bands. Nebulizers often use glass or plastic ampoules or blisters. As mentioned above, information regarding the type of drug in these containers is often printed directly on the container or on labels attached to them so that the patient or the doctor can read what kind of drug and strength the container is filled with, which may cause problems as discussed above. The above-mentioned problems can be even worse due to the fact that a medicament regimen in many cases requires more than one medicament as part of the regimen. For example, patients having diabetes take a combination of slow and fast acting types of insulin and it is important that the patient does not receive the incorrect medicament, i.e. that the medicaments do not become confused by mistake. As an example, medication cartridges have been used with injectors (for example, pen-type injectors) and are prevalently used in reusable or multi-dose devices for invasive delivery of medication. However, in a pen-type injector, a cartridge is inserted into the injector and used to provide an injection. The injector does not have any method of determining whether the medication cartridge is properly inserted or what type of medication is contained in the cartridge. The user must manually check the cartridge for proper insertion and must be sure that the medication is the right one, for example, whether the cartridge contains insulin of a slow or fast acting type. This is important, since improper insertion can result in the administration of an incorrect dosage of medication, which could result in injury or death. In addition, the user must know what type of medication is being used, since there are often different dosing requirements for different concentrations of the same medication. A number of different attempts have been made in order to solve these problems.

U.S. Pat. No. 3,503,493 discloses such a medicament packaging device for dispensing of medicaments unit dosages in tablet form comprising identification means. The identification means includes on one side pre-printed indicia concerning the drug contained within the unit dose package. At the other side of the identification means is an adhesive-coated surface arranged and thereby the identification means can be adhered to a document surface for documentation. The user, i.e. a nurse, a doctor, an assistant or a patient, must manually check the identification means in order to verify that a proper medicament is administered to the patient. Accordingly, for example, a nurse, a doctor, an assistant or a patient can misinterpret or misread the indicia of the identification means, which may lead to that the patient is administered with an incorrect medicament.

U.S. Pat. No. 5,377,839 discloses such a medicament dosing system which includes a reusable integral patient dispensing frame which supports a plurality of reusable cartridges. Replaceable blister packages having a plurality of individually sealed spaced pockets can be inserted into the cartridge. The system provides for organization by patient (e.g. alphabetically by name, location etc.) time (e.g. am, pm, noon, hour of sleep, etc). The user, i.e. a nurse, or a doctor, or a patient, must manually insert the blister packages and must organize the packages. Accordingly, for example, a nurse, a doctor, or a patient can insert a blister package containing an incorrect medicament due to, for example, misinterpretation or misreading of the information provided on the package, which may lead to that the patient is administered with an incorrect medicament.

In WO 94/16759 a detection system for an inhaler is disclosed. The system comprises an inhaler arranged with a compartment adapted to releasable receive a cassette with a certain shape. The cassette is provided with a number of protrusions arranged in a specific pattern on its outer surface, a so called multi-bit code. The protrusions have to mate with a corresponding slotted disc or key-plate in order for the device to function. The cassette contains, in turn, an aerosol container with medicament. The multi-bit words represented by the protrusions may be used to identify information such as type of drug, number of doses contained, time between doses, when the dose is to be delivered during inhalation, duration of the release and such. The inhaler body contains micro-switches which are pressed by the protrusions. The combination is checked against a library of stored delivery protocols in a storage means of the inhaler and the corresponding protocol is loaded into the electronics of the inhaler. Instead of protrusions the cassette may be provided with active or passive electronic circuit elements, such as impedance values, digital code-words or memory devices. The electronic circuit is electrically connected to the inhaler electronics. One major problem with this system is that the information is arranged on the cassette and not on the drug container itself. This leads to a rather expensive solution with an extra cassette. The electronic circuits also contribute to the fact that the solution will be rather expensive. A further problem is that it is possible to replace the aerosol canister in the cassette, not very easily but yet fully feasible, to another canister containing, for example, another drug. The information provided on the cassette in form of the protrusions would then be misleading. A further drawback with the system disclosed in WO 94/16759 is that the cassette containing the information needs to be physically connected to electrical and/or electronic means in the inhaler in order to for the system to be operable. Dirt, debris and the like may disturb the electrical connection, whereby the inhaler is rendered non-functional. In addition, the cassette and the contacting means increase the overall size of the inhaler.

WO 03/047665 discloses a combination of a medicament delivery apparatus and a medicament cartridge where the medicament delivery apparatus includes switches and the medicament cartridge comprises a raised ring about an external periphery of the medicament cartridge, the ring having dimensions to trip at least one of the switches. The location along a longitudinal axis of the cartridge as well as shape and colour of the ring provide an indication of the medicament contained within the cartridge. If the ring does not trip a specific switch connected to a processor, the medication delivery apparatus will not function. Thus, if a cartridge containing an incorrect medication is inserted into the apparatus, the apparatus will not function. In such a case, the patient is forced to remove the cartridge from the apparatus again in order to verify that the cartridge actually contained an incorrect medication since there may be a possibility that the apparatus itself does not function in a proper way, for example, due to a defect in the electronic circuits (e.g. the processor) of the apparatus. For patients, for example, having an impaired vision it may be difficult to tell whether a cartridge containing an incorrect medication was inserted into the apparatus or the apparatus itself does not function in a proper way. This is consequently not an ideal solution in a user friendly sense of meaning. Furthermore, due to the fact that, if a cartridge containing an incorrect medicament has been inserted into the apparatus and the apparatus accordingly does not function, the patient nevertheless has to remove the cartridge in order to verify that the inserted cartridge actually contains an incorrect medicament, the solution offered by WO 03/047655 is not an optimal solution in a risk management point of view.

U.S. Pat. No. 5,611,783 discloses a pen shaped syringe comprising a proximal part which may comprise a container and a distal part containing a dose setting and drive mechanism. The proximal and distal parts have interlocking bayonet coupling means. A mechanical coding as protrusions may be provided to form a pattern ensuring that a certain distal part may only be used in connection with a certain proximal part. The mechanical coding is provided between a dose assembly and a container holder.

WO 03/017915 discloses a container having a proximal end provided with a mechanical coding. The mechanical coding has the form of a circular protrusion where the circular outer diameter is dedicated a specific concentration of insulin contained in the container. In this way only a container containing the correct concentration or a lower concentration fits into a delivery system designed for a specific concentration of insulin. The mechanical coding is provided between the container and a container holder.

WO2008/025772, WO208/062065, WO2008/009645, WO2008/009647 and WO2008/000827 disclose containers having a distal end provided with a mechanical coding and a dose assembly provided with a corresponding mechanical coding for eliminating cross use of the dose assembly and the container. The mechanical coding is provided between a container and a dose assembly.

EP0941133 discloses a drug cartridge assembly having a mechanical coding for use with a reusable pen body assembly of a medication delivery pen having a corresponding mechanical coding. The mating members of the mechanical coding are selected so as to prevent cross-use with other assemblies, e.g., the pitch of the threads may be angled so as to mate only with one another and not with other assemblies. The mechanical coding is provided between a container and a dose assembly.

U.S. Pat. No. 5,693,027 discloses a plastic top for adapting a standard cartridge of the kind having a neck with a flange to a chosen syringe. This plastic top has a bore for receiving the neck part of the cartridge, which bore has a diameter making it fit over the metal cover and is provided with protrusions gripping behind the edge of the metal cover when the neck part is inserted in the bore. The outer contour of the plastic top is adapted to the syringe type in which the cartridge is going to be used. The plastic top is provided with a thread coaxial with the bore to receive a needle hub.

WO2008/009646 discloses a ring shaped element provided with a first mechanical coding and a second mechanical coding, wherein said first mechanical coding is arranged to cooperate with a corresponding mechanical coding of a dose assembly and wherein said second mechanical coding is arranged to cooperate with a corresponding coding of a medicament container.

WO2008/059063 discloses a ring shaped element provided with fastening means and a mechanical coding, wherein said fastening means are arranged to cooperate with corresponding fastening means of a container holder and said mechanical coding is arranged to cooperate with a corresponding mechanical coding of a dose assembly.

While there have been proposed a variety of medicament delivery systems including different types of identification solutions, such as described above, each have their own shortcomings, some of which have been detailed above, as well as shortcomings being universal for all the above-described systems. Generally, heretofore, there has not been available a single concept which solves the above-mentioned problems.

Therefore it is an object of the present invention to provide an alternative to the know systems wherein the coding has a higher degree of security.

SUMMARY OF THE INVENTION

A main object of the present invention is to provide a medicament delivery device comprising a generally tubular distal housing part having opposite proximal and distal ends, wherein third mechanically coded interface means are arranged on its proximal end; a generally tubular proximal housing part having opposite proximal and distal ends and being releasibly connected to said distal housing part, wherein with fourth mechanically coded interface means are arranged on its distal end; a medicament container having a slidable stopper, wherein said container is arranged to be positioned within said proximal housing part; a plunger rod arranged within said distal housing; drive means arranged within said distal housing and being operably connected to said plunger rod for driving said plunger rod and thereby said stopper towards the proximal end of the device; wherein said device further comprises an interface member comprising first and second mechanically coded interface means arranged to match and interact with the third and the fourth mechanically coded interface means when the distal and the proximal housing parts are connected to each other.

A further object of the invention is that said first mechanically coded interface means are arranged to match and interact with third mechanically coded interface means arranged on the distal housing part, and wherein said second mechanically coded interface means are arranged to match and interact with fourth mechanically coded interface means arranged on the proximal housing part.

Another object of the present invention is that said interface member is fixedly connected to the medicament container.

Other aspects according to the further and the another object of the present invention are that said first and second mechanically coded interface means are arranged on the outer surface of the interface member; that said third mechanically coded interface means are arranged on the proximal inner surface of the distal housing part, and that said fourth mechanically coded interface means arranged on the distal inner surface of the proximal housing part.

A further aspect according to the further and the another object of the present invention is that the proximal end of the distal housing part comprises second fastening means on its outer surface and the distal end of the proximal housing part comprises first fastening means on its inner surface, such that said distal housing part and said proximal housing part may be fastened to each other by said first and second fastening means when said first and third mechanically coded means and said second and fourth mechanically coded means comes into contact and match with each other; or that wherein the fourth and the third mechanically coded interface means comprises corresponding fastening means, such that the proximal and the distal housing parts may be fastened to each other; or that the first and the second mechanically coded interface means comprises fastening means that interfaces with corresponding fastening means of the third and the fourth mechanically coded interface means, such that the proximal and the distal housing parts may be connected to each other.

Yet another object of the present invention is that said interface member is instead releasibly connected to both said proximal and distal housing parts.

Other aspects according to the yet another object of the present invention are that said fourth mechanically coded interface means are arranged on the distal outer surface of the proximal housing part; that the first and the second mechanically coded interface means are arranged on the inner surface of the interface member; and that the third mechanically coded interface means are arranged on the proximal outer surface of the distal housing part.

A further aspect according to the yet another object of the present invention is that the third mechanically coded interface means are instead arranged on a second interface member having a ring-formed configuration and wherein the second interface member is releasibly attached to the proximal end of the distal housing, such that the third mechanically coded interface means protrudes through a transversal slot on the proximal end of the distal housing.

Other aspect according to the yet another object of the present invention is that the third mechanically coded interface means are arranged to match and interact with the fourth mechanically coded interface means, and that the first and second mechanically coded interface means are attachment means that interacts with corresponding attachment means on the outer surface of both the proximal and distal housing parts when the third and the fourth mechanically coded interface means match and interact with each other.

Still another aspect according to the yet another object of the present invention is that is to the proximal end of the distal housing part comprises first fastening means adapted to cooperate with corresponding second fastening means on the inner surface on the interface member when the first mechanically coded interface means match and interact with the third mechanically coded interface means.

Still other objects of the present invention are that each of the mechanically coded interface means comprises either male or female mating means, or a combination of both male and female mating means; and that each of the mechanically coded interface means has a predetermined degree of geometry and mechanically match as geometrical form and dimension.

For purposes of clarity, the term "correct medicament container" can refer to, inter alia, a medicament container having intended medicament strength, amount (or dose), or kind of medication, as well as time between doses, maximum or minimum time between doses. Accordingly, the term "incorrect medicament container" can refer to a medicament container having an incorrect strength, amount (or dose), or kind of medication, as well as incorrect time between doses, incorrect maximum or minimum time between doses. The term medicament container assembly refers to a medicament container arranged within a proximal housing part/container holder. The term power pack refers to the distal housing part and all the technical features and technical means that are arranged within it.

This solution provides several advantages over the conventional techniques. One advantage is that a user, for example, a patient is provided with two clear and distinct indications. The first indication is whether the medicament container comprising the interface member he or she tries to connect to the proximal housing part is correct or not, or whether the medicament container assembly, he or she tries to connect to the interface member is correct or not. After the first indication is correct, the second indication is whether the medicament container assembly comprising the medicament container with the interface member or the medicament container assembly correct connected to the interface member, he or she tries to connect to the power pack is correct or not. That is, the power pack only accepts the correct medicament container assembly since the user, for example, the patient cannot connect the power pack to the medicament container assembly without using unduly force or without manipulating any of the housings of the medicament delivery device, the interface member, using, for example, a tool. Thereby, the safety of the patient can be improved.

Another advantage of the present invention is that it can be secured that only, for example, a medicament container from a certain producer can be used in with a correct medicament delivery device, since, for example, containers containing the medicament from the certain producer can be arranged such that only these containers arranged with an interface member or container assemblies interacting with an interface member disclose a clear degree of geometrical and mechanical match between the interface member and the housings of the medicament delivery device.

A further advantage of the present invention is that the mechanically coded interface means that are arranged on the power pack may be provided on a detachable part for the purpose of manufacturing a same power pack for all mechanically coded interface members, but which can be assembled with different detachable parts, wherein each different detachable part comprises a different mechanical interface means that only matches and interacts with the correct interface member.

The features that characterize the invention, both as to organization and to method of operation, together with further objects and advantages thereof, will be better understood from the following description used in conjunction with the accompanying drawings. It is to be expressly understood that the drawings is for the purpose of illustration and description and is not intended as a definition of the limits of the invention. These and other objects attained, and advantages, offered by the present invention will become more fully apparent as the description that now follows is read in conjunction with the accompanying drawings.

BRIEF DESCRIPTION OF DRAWINGS

In the following detailed description of the invention, reference will be made to the accompanying drawings, of which

DETAILED DESCRIPTION OF THE INVENTION

In the present application, when the term "distal part/end" is used, this refers to the part/end of the delivery device, or the parts/ends of the members thereof, which is/are located the furthest away from the medicament delivery site. Correspondingly, when the term "proximal part/end" is used, this refers to the part/end of the delivery device, or the parts/ends of the members thereof, which, is/are located closest to the medicament delivery site.

Figure 4:
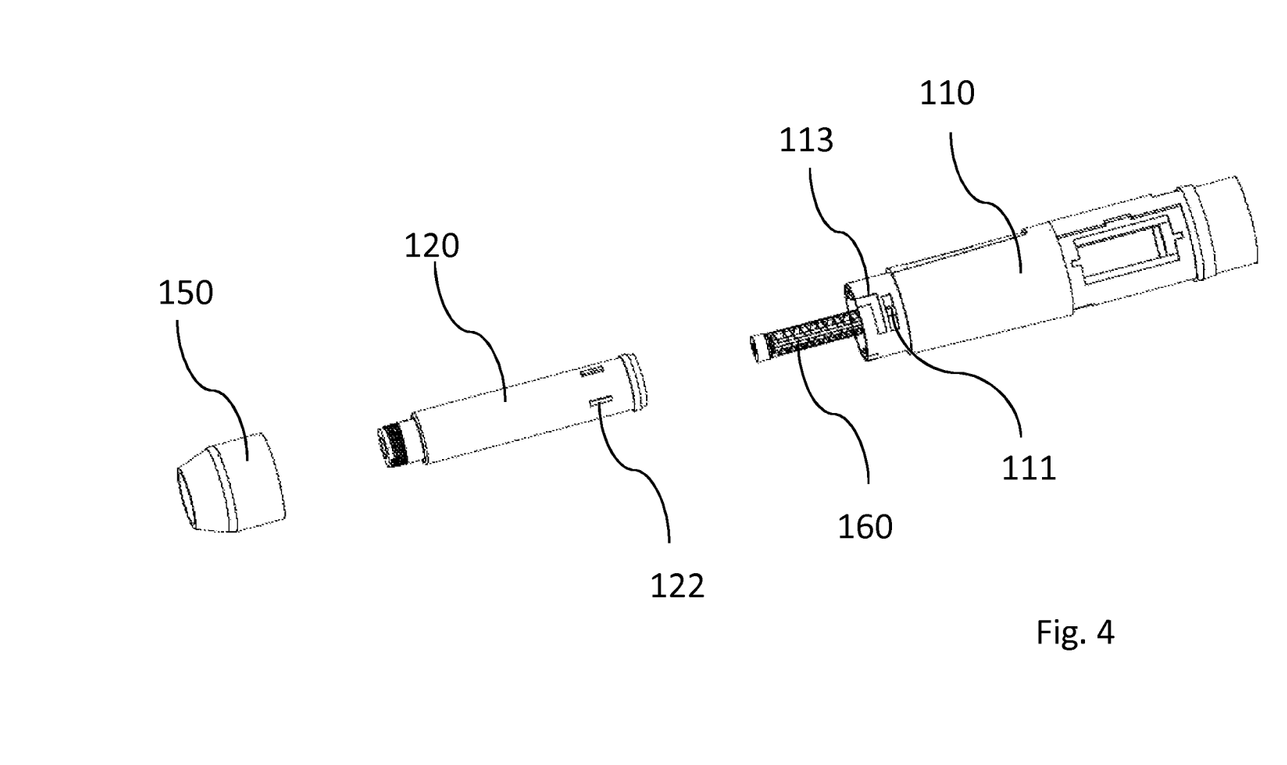
FIG. 4, illustrates an exploded perspective view of a second embodiment according to the present invention showing a distal housing, a proximal housing, a plunger rod and an interface member.

The present invention relates to a medicament delivery device comprising a generally tubular distal housing part 10; 110 having opposite proximal and distal ends, wherein third mechanically coded interface means 11; 111 are arranged on its proximal end; a generally tubular proximal housing 20; 120 part having opposite proximal and distal ends and being releasably connected to said distal housing part, wherein with fourth mechanically coded interface means 22; 122 are arranged on its distal end; a medicament container having a slidable stopper, wherein said container is arranged to be positioned within said proximal housing part; a plunger rod 60; 160 having a distal end arranged within said distal housing, where, as illustrated in FIG. 4, the distal end remains within the distal housing part when the proximal and distal housing parts are disconnected and completely separated from each other; drive means arranged within said distal housing and being operably connected to said plunger rod for driving said plunger rod and thereby said stopper towards the proximal end of the device; wherein said device further comprises an interface member 50; 150 comprising first 51; 151 and second 52; 152 mechanically coded interface means arranged to non-threadedly match and interact with the third 11; 111 and the fourth 22; 122 mechanically coded interface means when the distal and the proximal housing parts are connected to each other. Interface member 50 is preferably completely contained and arranged within both the distal and proximal housing parts 10, 20. Additionally, it is preferred that that the interface member is releasably connected to both the proximal and distal housing parts and forms no part of the drive mechanism.

Further, the first mechanically coded interface means 51; 151 are arranged to match and interact with third mechanically coded interface means 11; 111 arranged on the distal housing part, and wherein said second mechanically coded interface means 52; 152 are arranged to match and interact with fourth mechanically coded interface means 22; 122 arranged on the proximal housing part.

Figure 1:
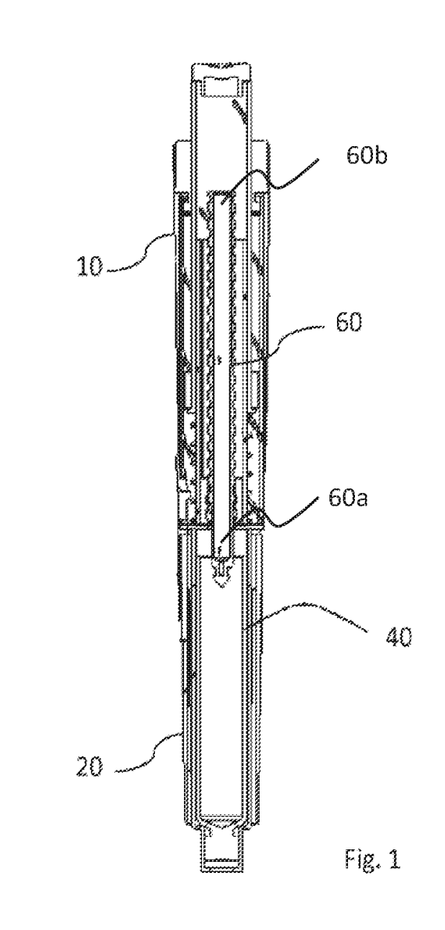
FIG. 1 illustrates a medicament delivery device according to the present invention.

In FIG. 1 is shown a medicament delivery device as a generally elongated injector. The proximal housing part is a medicament container holder 20 capable of housing the container 40 e.g. a cartridge, a syringe, or the like. The delivery device has a plunger rod 60 having a proximal end 60a and a distal end 60b. The container holder is releasibly attachable to the distal housing part 10 of the injector, which arranges the plunger rod 60 and the drive means. The distal end 60b is completely contained and arranged within distal housing part 10. The drive means may also include dose setting means and actuating delivery means. It is also to be understood that the medicament delivery device may be a pen-injector, an auto-injector, or any other kind of medicament delivery devices that comprises a distal and proximal housing parts that has to be connected and fastened to each other.

Figure 2:
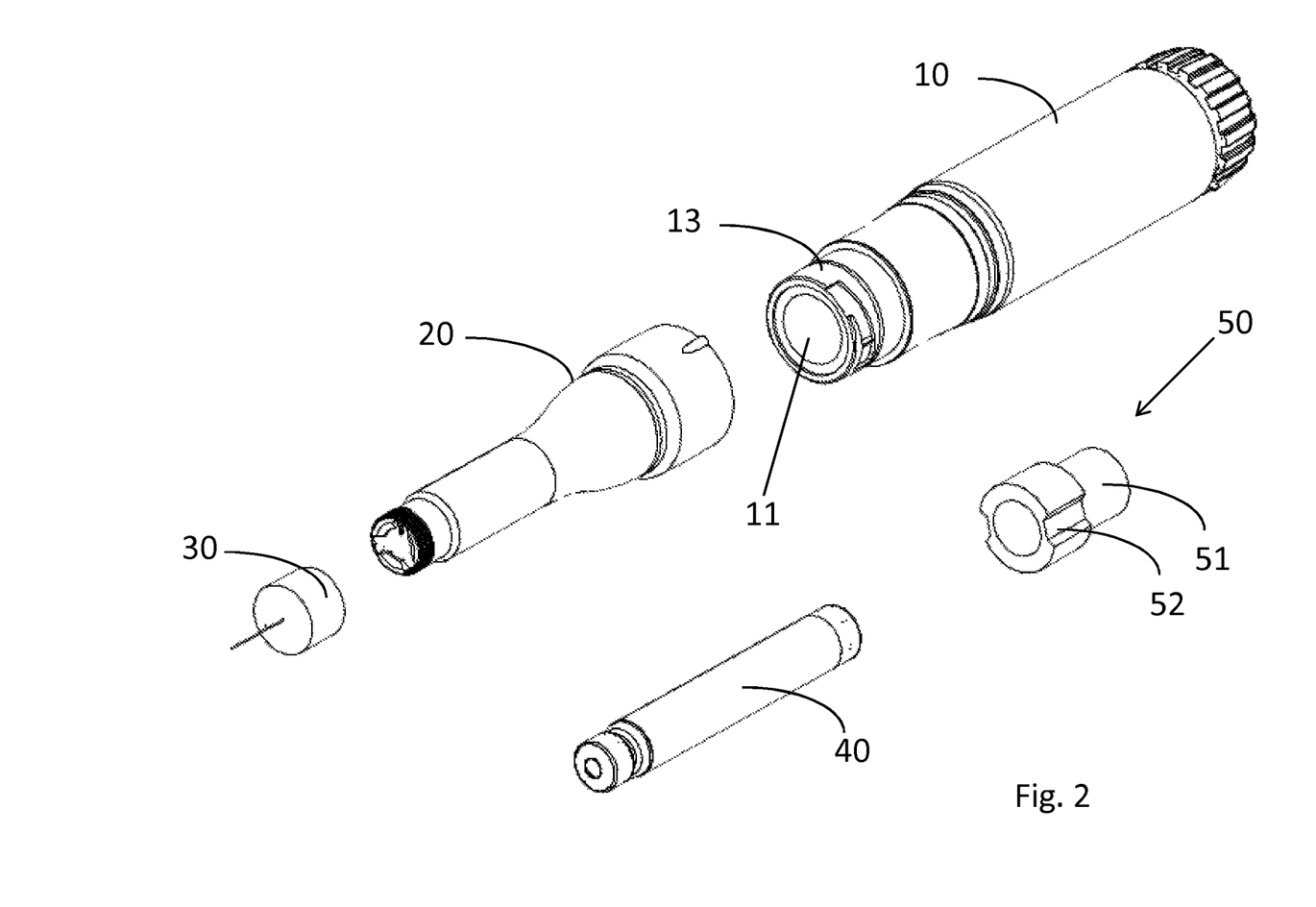
FIG. 2 illustrates an exploded perspective view of a first embodiment according to the present invention showing a distal housing, a proximal housing, a container, a delivery member and an interface member.
Figure 3:
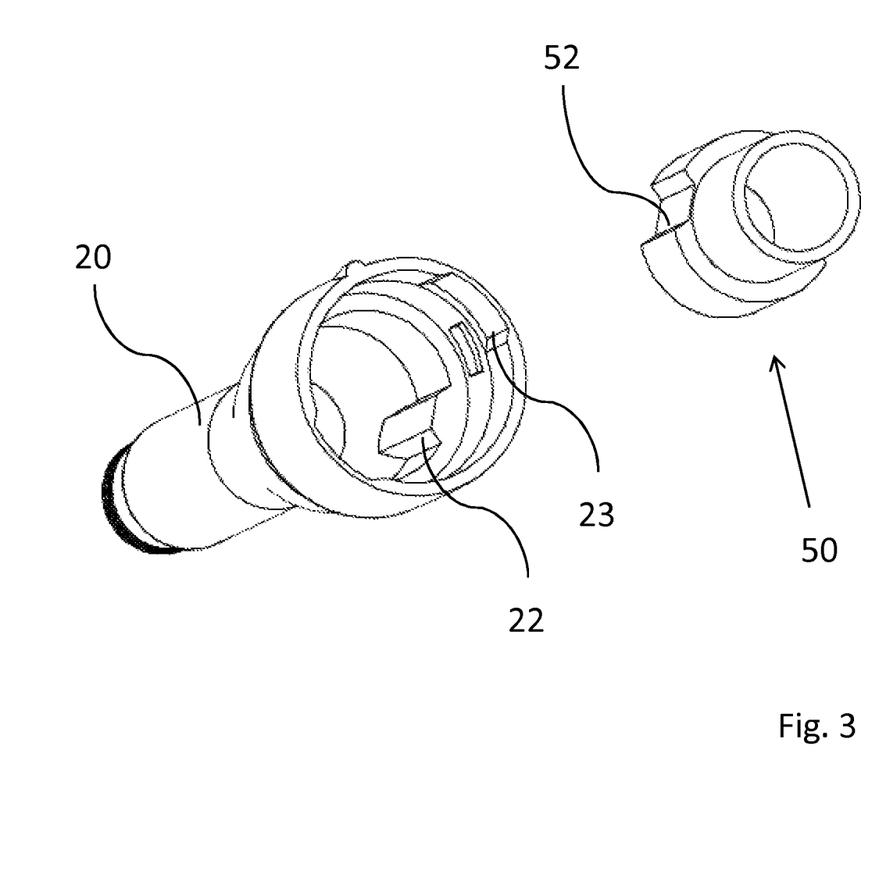
FIG. 3, illustrates a perspective view of the proximal housing and of the interface member seen from a distal view according to the first embodiment.

In a first embodiment as shown in FIGS. 2 and 3, the medicament delivery device comprises the interface member 50 having a sleeve-formed configuration. The outer surface of the interface member comprises the first mechanically coded interface means 51 and the second mechanically coded interface means 52. The interface member 50 is completely contained and arranged within both the distal and proximal housing parts, is not connected to the plunger rod, and is arranged to be fixedly attached and surrounding the container 40 such as a syringe, cartridge or the like by gluing, soldering or by other known process. The interface member is made of a material such that if an attempt to remove said interface member from said container is performed, said interface member is deformed. The distal end of the proximal housing part comprises first fastening means 23, FIG. 3, on its inner surface adapted to cooperate with corresponding second fastening means 13, FIG. 2, on the outer surface on the proximal end of the distal housing, wherein the second fastening means is formed as a unitary, one-piece construction. The proximal housing part is adapted to receive the container having the interface member. The distal inner surface of the proximal housing part comprises the fourth mechanically coded interface means 22, FIG. 3, arranged to match the second mechanically coded interface means 52 when the container with the interface member is placed within the proximal housing part. The proximal inner surface of the distal housing comprises the third mechanically coded interface means 11, FIG. 2, arranged to match the first mechanically coded interface means 51, FIG. 2, of the interface member such that the first fastening means 23 of the proximal housing part and the second fastening means 13 of the distal housing part may contact each other for fastening said proximal housing part to said distal housing part.

In FIG. 2 is also shown a delivery member 30 as pen needle having attachment means as threads, bayonets, luer lock or the like, on its inner surface which are arranged to cooperate with corresponding attachment means on the proximal outer surface of the proximal housing part.

A variant of the first embodiment (not shown) is that neither the proximal end of the distal housing part nor the distal end of the proximal housing comprises fastening means. Instead, the fourth and the third mechanically coded interface means comprises corresponding fastening means such as bayonet fixings, such that the proximal and the distal housing parts may be fastened to each other.

Another variant of the first embodiment (not shown) is that neither the proximal end of the distal housing part nor the distal end of the proximal housing comprises fastening means. Instead, the first and the second mechanically coded interface means comprises fastening means that interfaces with corresponding fastening means of the third and the fourth mechanically coded interface means, such that the proximal and the distal housing parts may be connected to each other.

Still another variant of the first embodiment (not shown) is that neither the proximal end of the distal housing part nor the distal end of the proximal housing comprises fastening means. Instead, an attachment ring comprising attachment means on its inner surface interact with corresponding attachment means on the outer surface of both the distal and proximal housing parts.

A further variant of the first embodiments is that the container is manufactured comprising the interface member 50.

Figure 5:
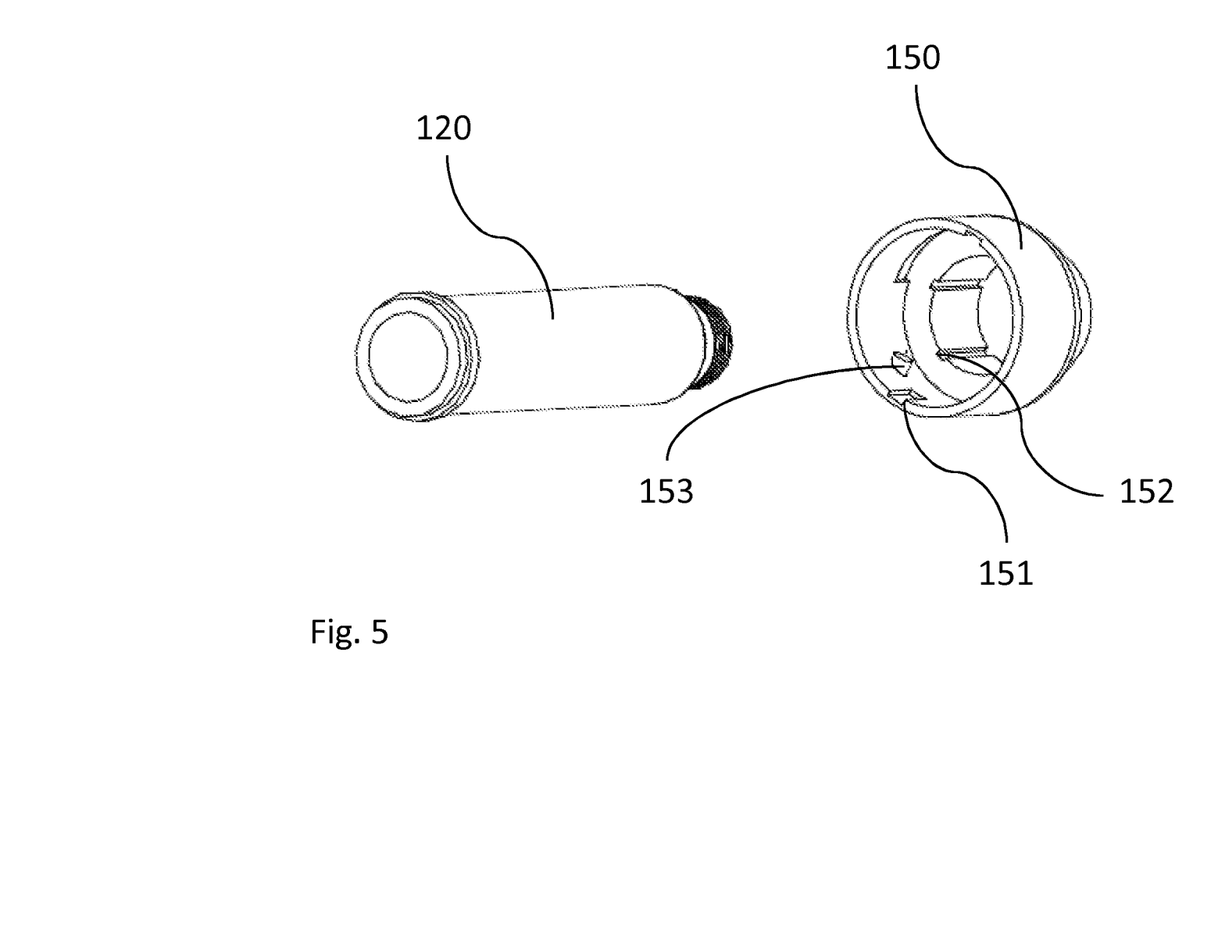
FIG. 5, illustrates a perspective view of the proximal housing and of the interface member seen from a distal view according to the second embodiment.
Figure 6:
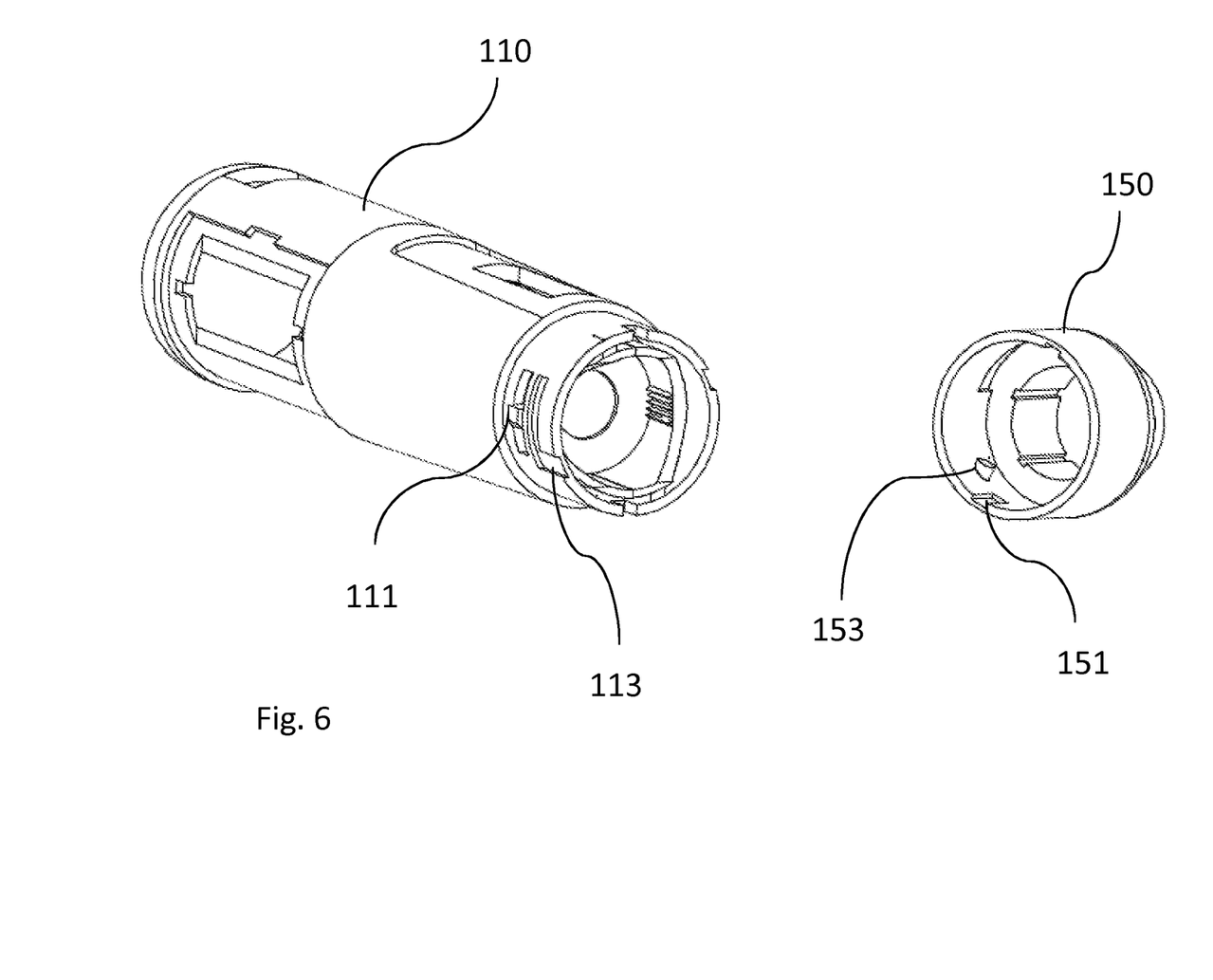
FIG. 6, illustrates a perspective view of the distal housing and of the interface member according to the second embodiment.

In a second embodiment as shown in FIGS. 4-6, the medicament delivery device comprises the interface member 150 having a sleeve-formed configuration. Said interface member is releasibly connected to both said proximal 120 and distal 110 housing parts. As shown in FIG. 5, the inner surface of the interface member 150 comprises the first mechanically coded interface means 151 and the second mechanically coded interface means 152. The container is fixedly arranged inside the proximal housing part 120. The distal outer surface of the proximal housing part comprises the forth mechanically coded interface means 122 arranged to match the second mechanically coded interface means 152 when the proximal housing part is proximally passed through the interface member until the interface member is rotationally locked to the proximal housing part such that the proximal housing is prevented of being further moved towards the proximal end of the device. Further, the proximal end of the distal housing part comprises first fastening means 113, FIG. 4, adapted to cooperate with corresponding second fastening means 153, FIG. 6, on the inner surface on the interface member 150 when the first mechanically coded interface means 151 match and interact with the third mechanically coded interface means 111 arranged on the proximal outer surface of the distal housing.

Figure 7:
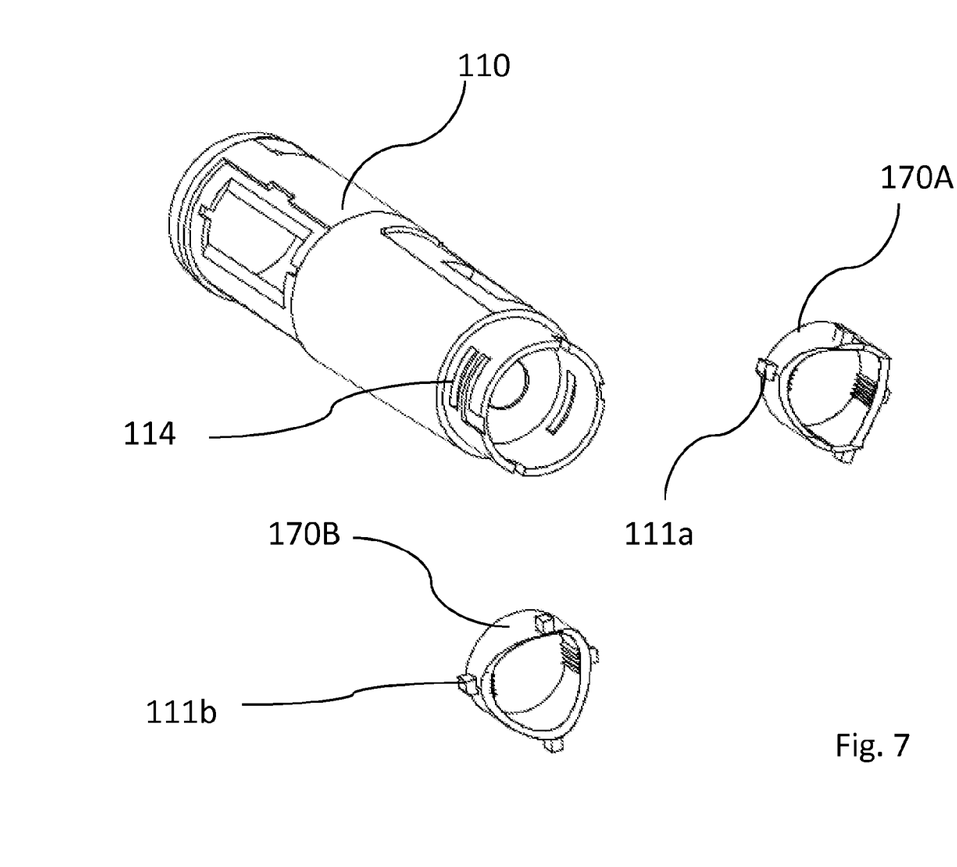
FIG. 7, illustrates a perspective view of the distal housing and of a second interface member according to the second embodiment.

A variant of the second embodiment, as shown in FIG. 7, is that the third mechanically coded interface means 111a, 111b are arranged on a second interface member 170A, I 70B having a ring-formed configuration. The second interface member is releasibly attached to the proximal end of the distal housing, such that the third mechanically coded interface means 111a, 111b protrudes through a transversal slot 114 on the proximal end of the distal housing.

A further variant of the second embodiment (not shown) is that wherein the third 111 mechanically coded interface means are arranged to match and interact with the fourth 122 mechanically coded interface means, and that the first 151 and second 152 mechanically coded interface means are attachment means that interacts with corresponding attachment means on the outer surface of both the proximal and distal housing parts when the third and the fourth mechanically coded interface means match and interact with each other.

Each mechanically coded interface means of the interface member is arranged to mate each corresponding mechanically coded interface means of the proximal housing part and of the distal housing part in a clear and distinct way establishing a clear geometrical and mechanical identification interface between the interface member and both the proximal housing part and the distal housing part, such that a user/patient cannot use an erroneous container/container holder in a distal housing part as described above and which is predetermined for expelling a different kind of medicament that is arranged in the container.

It is to be understood that each of the mechanically coded interface means comprises either male or female mating means, or a combination of both male and female mating means. It is also to be understood that each of the mechanically coded interface means comprises a predetermined degree of geometry and mechanical match as geometrical form and dimension.

Furthermore, the mechanically coded interface means can also be spring-loaded by means of a spring element (not shown).

It is to be understood that the embodiment described above and shown in the drawing is to be regarded only as a non-limiting example of the invention and that it may be modified in many ways within the scope of the patent claims.

The invention claimed is:
1. A medicament delivery device, comprising:
   a generally tubular distal housing part having opposite proximal and distal ends, wherein the proximal end of the distal housing part comprises a second fastener formed as a unitary, one-piece construction of an outer surface of the proximal end of the distal housing part and a third mechanically coded interface device located on an inner surface of the proximal end of the distal housing part;
   a generally tubular proximal housing part having opposite proximal and distal ends and releasably connected to the distal housing part through mechanical engagement of the second fastener with a first fastener, where the first fastener is located on an inner surface of the distal end of the proximal housing part along with a fourth mechanically coded interface device also located on the inner surface of the distal end of the proximal housing part, and where the first fastener and the second fastener contact and cooperate with each other to result in a secure fastened connection between the distal housing part and the proximal housing part such that the distal and proximal housing parts are releasably locked together;
   a medicament container having a slidable stopper, where the medicament container is arranged to be completely positioned and contained within the proximal housing part;
   a drive mechanism comprising a plunger rod having a distal end, where the distal end of the plunger rod is completely contained and arranged within the distal housing part, the drive mechanism operably configured for driving a proximal end of the plunger rod from the distal housing part into the proximal housing part and into the medicament container to drive the stopper toward a proximal end of the medicament delivery device, where the distal end of the plunger rod remains within the distal housing part when the proximal and distal housing parts are disconnected and completely separated from each other; and wherein an interface member is completely contained and arranged within both the distal and proximal housing parts when the distal and proximal housing parts are connected to each other, and wherein the interface member is not connected to the plunger rod, and forms no part of the drive mechanism, the interface member comprises first and second mechanically coded interface devices arranged to match and interact with the third and the fourth mechanically coded interface devices when the distal and proximal housing parts are connected to each other, wherein the interface member is releasably connected to both the proximal and distal housing parts; the first and second mechanically coded interface devices non-threadedly mate with the third and fourth mechanically coded interface devices to establish a geometrical and mechanical identification interface between the interface member and the proximal and distal housing parts that precludes use of an erroneous medicament container or medicament.

2. The medicament delivery device of claim 1, wherein the first mechanically coded interface device is arranged to match and interact with the third mechanically coded interface device arranged on the distal housing part, and the second mechanically coded interface device is arranged to match and interact with the fourth mechanically coded interface device arranged on the proximal housing part.

3. The medicament delivery device of claim 1, wherein the interface member is fixedly connected to a distal end of the medicament container such that an attempted removal of the interface member will deform the interface member.

4. The medicament delivery device of claim 1, wherein the proximal end of the distal housing part includes the second fastener on its outer surface and the distal end of the proximal housing part includes the first fastener on its inner surface, such that the distal housing part and the proximal housing part can be fastened to each other by the first and second fasteners when the first and third mechanically coded devices and the second and fourth mechanically coded devices come into contact and match with each other.

5. The medicament delivery device of claim 1, wherein the fourth mechanically coded interface device is configured as a male shaped component and the third mechanically coded interface device is configured as a female shaped component, such that when the fourth and third mechanically coded interface devices are mated and matched geometrically, respectively, to the second and first coded interface devices, the proximal and the distal housing parts can be fastened to each other.

6. The medicament delivery device of claim 1, wherein the first and second mechanically coded interface devices are configured with the third and the fourth mechanically coded interface devices to fasten the proximal and the distal housing parts to each other.

7. The medicament delivery device of claim 1, wherein each mechanically coded interface device includes at least one of a male mating device and a female mating device.

8. The medicament delivery device of claim 1, wherein each mechanically coded interface device includes a predetermined degree of geometry and mechanical match as geometrical form and dimension.

* * * * *